United States Patent
Zucchi

[11] Patent Number: 5,592,933
[45] Date of Patent: Jan. 14, 1997

[54] HYGROSCOPIC CARTRIDGE PARTICULARLY FOR FILTERS FOR MEDICAL USE

[75] Inventor: Giuseppe Zucchi, San Possidonio, Italy

[73] Assignee: Mallinckrodt Medical, Inc., St. Louis, Mo.

[21] Appl. No.: 374,557

[22] PCT Filed: Jul. 19, 1993

[86] PCT No.: PCT/EP93/01899

§ 371 Date: Mar. 23, 1995

§ 102(e) Date: Mar. 23, 1995

[87] PCT Pub. No.: WO94/02192

PCT Pub. Date: Feb. 3, 1994

[30] Foreign Application Priority Data

Jul. 22, 1992 [IT] Italy .................................. MI92A1777

[51] Int. Cl.$^6$ ............................. A61M 16/00; A62B 9/00
[52] U.S. Cl. ................................... 128/201.13; 128/205.27
[58] Field of Search ......................... 128/201.13, 205.27, 128/204.13, 204.17; 261/5, 6, 152–157, DIG. 72; 428/182–185; 55/241, 257.2, 257.7, 257.3, 259; 165/60

[56] References Cited

U.S. PATENT DOCUMENTS

| | | | |
|---|---|---|---|
| 3,433,692 | 3/1969 | Gewiss | 156/196 |
| 4,497,753 | 2/1985 | Streif | 261/95 |
| 5,384,178 | 1/1995 | Rye | 428/182 |

Primary Examiner—V. Millin
Assistant Examiner—Eric P. Raciti
Attorney, Agent, or Firm—David A. Hey

[57] ABSTRACT

The hygroscopic cartridge (1) particularly for filters for medical use, has a band-like element (2) which is wound to form a flat bobbin (7). The band-like element (2) has a first band (3), formed with corrugations (4) which extend in a transverse direction with respect to the longitudinal extension of the band-like element (2) and made of a heat-conducting plastically deformable material, and a second layer (5) impregnated with hygroscopic salts. The corrugations (4) define small channels (8) for allowing the passage of an aeriform flow in a transverse direction with respect to the plane of lay of the flat bobbin (7).

3 Claims, 1 Drawing Sheet

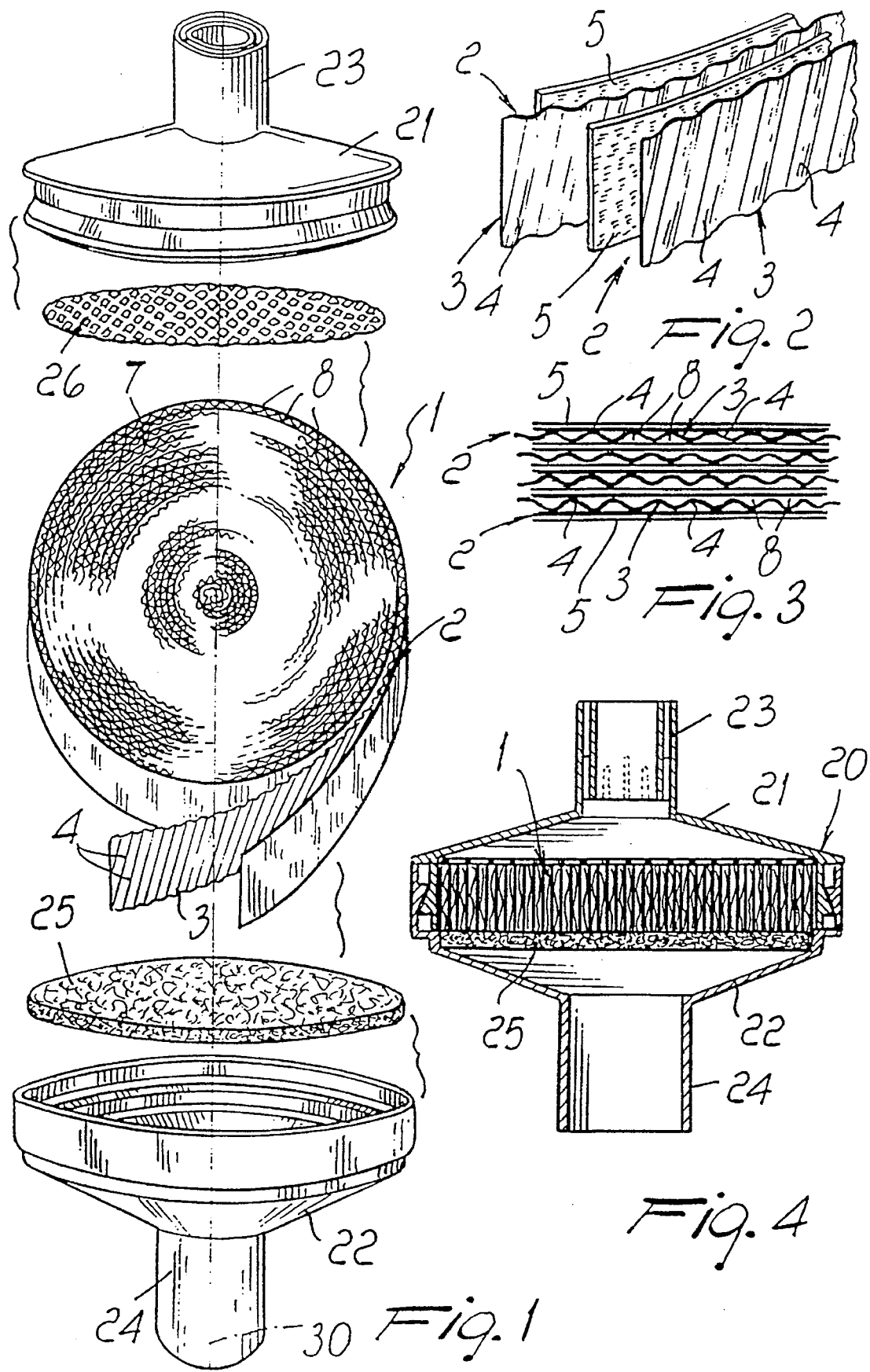

HYGROSCOPIC CARTRIDGE PARTICULARLY FOR FILTERS FOR MEDICAL USE

TECHNICAL FIELD

The present invention relates to a hygroscopic cartridge particularly for filters for medical use.

BACKGROUND ART

As known, in many medical applications, and in particular in the fields of medicine and surgery, filters treated with hygroscopic salts are currently used. The filters are employed as humidifying elements to provide a respiration process which is similar to the normal physiological action of the respiratory tract.

Italian Patent Application No. 21794 A/90, filed on Oct. 19, 1990, discloses a hygroscopic cartridge for filters which is made substantially of a band constituted by first and second layers of paper impregnated with hygroscopic salts. The layers are superimposed and have mutually opposite corrugations forming a plurality of channels which extend transversely with respect to the plane of lay of the bobbin.

This type of filter, which has proved to be valid in some respects, is however not devoid of inconveniences. It is relatively difficult to manufacture since the channels are created by forming corrugations on paper bands and thus, during winding, the channels may be crushed such that the transverse cross sectional passage area of the channels is substantially reduced.

A further disadvantage resides in the fact that, during inhalation, air entering the filter creates a significant drop in the temperature of the filter cartridge, with a consequent increase in condensation and a reduction in the moisture content of the aeriform flow which the patient breathes.

DISCLOSURE OF THE INVENTION

Wiyh the foregoing and other objects in view, there is provided a hygroscopic cartridge particularly for filters for medical use, which permits the accumulation of heat in the filter during the exhalation phase with a successive release of heat during the inhalation phase, consequently increasing the humidity content of the aeriform inflow.

Within the above aim, an object of the present invention is to provide a hygroscopic cartridge having elements which impart a relatively stable configuration to the channels for the passage of the aeriform flow, employing means which are not susceptible to "crushing" even during the winding of the cartridge, thereby providing a correct transverse cross sectional passage for the aeriform flow.

Another object of the present invention is to provide a hygroscopic cartridge particularly for filters for medical use which, by virtue of its unique characteristics, is highly reliable and safe in use.

A further object of the present invention is to provide a hygroscopic cartridge particularly for filters for medical use which can be easily manufactured by using commercially available elements and materials.

BRIEF DESCRIPTION OF THE DRAWINGS

Further characteristics and advantages of the hygroscopic cartridge particularly for filters for medical use, will become apparent from the following description of a preferred but non-exclusive embodiment thereof, shown in the following illustrative non-limitative drawings wherein:

FIG. 1 is a schematic exploded perspective view of the cartridge according to the present invention, showing one embodiment of the filter;

FIG. 2 is a perspective view showing the overlapping of the layers;

FIG. 3 is a plan view showing the adjacent layers;

FIG. 4 is a sectional view of a filter incorporating a cartridge according to the present invention.

WAYS OF CARRYING OUT THE INVENTION

With reference to the above-mentioned drawing figures, the hygroscopic cartridge particularly for filters for medical use, according to the present invention, is generally designated by the reference numeral 1. The cartridge 1 comprises a band-like element 2 which is wound so as to form a flat bobbin 7 which may have any configuration, such as a circular, oval, or similar configuration.

An important characteristic of the present invention is constituted by the fact that the band-like element 2 has a first layer or tape 3 provided with a plurality of corrugations 4, which extend in a transverse direction with respect to the longitudinal extension of said band-like element. As clearly shown in FIG. 2, the corrugations 4 are advantageously constituted by mutually parallel undulations which are inclined with respect to the axis 30 of the bobbin 7. The corrugations 4 define small channels 8 which allow the passage of an aeriform flow through the cartridge 1.

The first layer 3 is made of a plastically deformable material, whereby to securely maintain the corrugations provided thereon. The material is also a good conductor of heat.

From experimental tests, it has been found that the first layer can advantageously be made of aluminium foil, though obviously, other materials may also be used which have analogous characteristics and which are compatible with the intended use.

A second layer or tape 5 having a flat configuration is provided adjacent to the first tape 3. The second tape 5 is impregnated with hygroscopic salts and is wound together with the first tape 3 to form the bobbin 7.

The bobbin 7 thus formed is advantageously housed within a filter body 20. The filter body 20 may be provided, for example, with a first half shell 21 and a second half shell 22 which are connected together and provided with conduits 23, 24. Absorbent pads 25 and retaining nets 26 can also be provided at opposite ends of the cartridge 1.

Providing the cartridge 1 with a layer of aluminium also has the advantage of rapidly absorbing heat from the aeriform flow during exhalation and accumulating heat in a very short time interval. In fact, the exhalation phase usually has a duration of one second and in this short time the layer 3 must absorb as much heat as possible.

The channels 8 defined by the corrugations enhance the accumulation of heat by causing strong turbulence in the aeriform flow. The accumulation of heat is indispensable for increasing the content of humidity within the filter, which is then exchanged with the dry gases passing through the filter during inhalation.

During inhalation, cold dry air entering from the outside is at least partially warmed by heat which is accumulated within the layer 3. In this way humidity is maintained at a higher level which facilitates the exchange of such humidity within the cartridge 1 towards the fresh gases that the patient inhales.

From the foregoing description it has been seen that the invention achieves the proposed aims. In particular, the fact is emphasized that the aluminium layer 3 with transverse corrugations 4 stably maintains the configuration of the layer with channels 8 which are uniformly distributed throughout the surface of the cartridge 1.

Furthermore, the use of a heat conductive material permits the accumulation, in a brief time, of heat from the exhaled aeriform flow which is exchanged successively with the inhaled aeriform flow.

In this way, the moisture content of the filter is increased and consequently the moisture content of the inhaled air is also increased. This renders the complete respiration cycle as similar to normal physiological respiration as possible.

The invention thus conceived is susceptible to numerous modifications and adaptations, all within the purview of the instant inventive concept.

Furthermore, all elements can be substituted by other technically equivalent elements.

In practice, any materials, shapes and dimensions that are compatible with the specific use may be used according to requirements.

Where technical features mentioned in any claim are followed by reference signs, those reference signs have been included for the sole purpose of increasing the intelligibility of the claims and accordingly, such reference signs do not have any limiting effect on the scope of each element identified by way of example by such reference signs.

I claim:

1. Hygroscopic cartridge particularly for filters for medical use, comprising a band-like element which is wound to form a flat bobbin, characterized in that said band-like element comprises a first layer, having corrugations which extend in a transverse direction with respect to the longitudinal extension of said band-like element and made of a heat-conducting plastically deformable material, and a second layer impregnated with hygroscopic salts, said corrugations defining channels for an aeriform flow in a transverse direction with respect to the plane of lay of the flat bobbin, wherein said corrugations are constituted by mutually parallel undulations, said undulations being inclined with respect to the longitudinal axis of said bobbin.

2. Hygroscopic cartridge according to claim 1, characterized in that said first layer is made of aluminium foil.

3. Filter for medical use, characterized in that it comprises a filter body provided with conduits and defining a portion for housing a hygroscopic cartridge constituted by a band-like element made of a first layer, having corrugations which extend in a transverse direction with respect to the longitudinal extension of said band-like element and made of a heat-conducting plastically deformable material, and a second layer impregnated with hygroscopic salts, said corrugations defining channels for an aeriform flow in a transverse direction with respect to the plane of lay of the cartridge, wherein said corrugations are constituted by mutually parallel undulations, said undulations being inclined with respect to the longitudinal axis of said cartridge.

\* \* \* \* \*